(12) United States Patent
Liu et al.

(10) Patent No.: US 11,944,685 B2
(45) Date of Patent: Apr. 2, 2024

(54) PREPARATION METHOD AND APPLICATION OF NOVEL INJECTION ABIRATERONE DERIVATIVE

(71) Applicant: TIANJIN HAIRUNJIAHE INNOVATIVE PHARMACEUTICAL RESEARCH LIMITED LIABILITY COMPANY, Tianjin (CN)

(72) Inventors: Tianjun Liu, Tianjin (CN); Na Zhu, Tianjin (CN); Yumei Rong, Tianjin (CN); Ge Hong, Tianjin (CN)

(73) Assignee: TIANJIN HAIRUNJAHE INNOVATIVE PHARMACEUTICAL RESEARCH LIMITED LIABILITY COMPANY, Tianji (CN)

( * ) Notice: Subject to any disclaimer, the term of this patent is extended or adjusted under 35 U.S.C. 154(b) by 0 days.

(21) Appl. No.: 18/280,132

(22) PCT Filed: Mar. 14, 2022

(86) PCT No.: PCT/CN2022/080603
§ 371 (c)(1),
(2) Date: Sep. 1, 2023

(87) PCT Pub. No.: WO2022/199408
PCT Pub. Date: Sep. 29, 2022

(65) Prior Publication Data
US 2024/0042041 A1    Feb. 8, 2024

(30) Foreign Application Priority Data

Mar. 25, 2021  (CN) .......................... 202110321653.X

(51) Int. Cl.
*A61P 35/00* (2006.01)
*A61K 9/00* (2006.01)
*A61K 47/54* (2017.01)

(52) U.S. Cl.
CPC .......... *A61K 47/543* (2017.08); *A61K 9/0019* (2013.01); *A61P 35/00* (2018.01)

(58) Field of Classification Search
CPC ...... A61K 47/543; A61K 9/0019; A61P 35/00
USPC ........................................... 514/176
See application file for complete search history.

(56) References Cited

FOREIGN PATENT DOCUMENTS

| | | | |
|---|---|---|---|
| CN | 102477061 | A | 5/2012 |
| CN | 102702140 | A | 10/2012 |
| CN | 102731442 | A | 10/2012 |
| CN | 103143013 | A | 6/2013 |
| CN | 103819429 | A | 5/2014 |
| CN | 108863992 | A | 11/2018 |
| CN | 109796519 | A | 5/2019 |
| CN | 113061154 | A | 7/2021 |
| WO | 2014111815 | A2 | 7/2014 |

OTHER PUBLICATIONS

International Search Report of PCT/CN2022/080603.
Written Opinion of PCT/CN2022/080603.

*Primary Examiner* — Yevgeny Valenrod

(57) ABSTRACT

Disclosed in the present disclosure are a novel injection polyaminopolycarboxylic acid-modified abiraterone derivative for treatment of prostate tumor, a pharmaceutical preparation containing the polyaminopolycarboxylic acid-modified abiraterone derivative, a preparation method, and an application. The polyaminopolycarboxylic acid-modified abiraterone derivative has the following structure (I). The polyaminopolycarboxylic acid-modified abiraterone derivative in the present disclosure has good water solubility, can be completely dissolved in an aqueous solution of sodium bicarbonate, is simple and convenient to prepare, high in yield, and suitable for large-scale production, has a remarkable effect in resisting tumors, can be used for treating prostate cancer tumor, and has the characteristics of high efficiency and low toxicity.

15 Claims, 12 Drawing Sheets

PREPARATION METHOD AND APPLICATION OF NOVEL INJECTION ABIRATERONE DERIVATIVE

CROSS-REFERENCE TO RELATED APPLICATIONS

This Application is a national stage application of PCT/CN2022/080603. This application claims priorities from PCT Application No. PCT/CN2022/080603, filed Mar. 14, 2022, and from the Chinese patent application 202110321653.X filed Mar. 25, 2021, the content of which are incorporated herein in the entirety by reference.

TECHNICAL FIELD

The present disclosure belongs to the field of organic synthesis and drugs, and particularly relates to a preparation method and an application of a novel injection polyaminopolycarboxylic acid modified Abiraterone derivative for treatment of prostate tumor, in particular to a novel injection polyaminopolycarboxylic acid modified Abiraterone derivative, prepared by reacting Abiraterone with polyaminopolycarboxylic acid monoanhydride and an application thereof in preparation of anti-tumor drugs.

BACKGROUND ART

Prostate cancer (PCa) is an androgen-dependent disease and ranks second among male malignant tumors worldwide, with a fatality rate second only to lung cancer. It exhibits strong pathological heterogeneity and has a 5-year survival rate of only 28%. In recent years, with an increasing aged tendency of population, change of lifestyle and popularization of Prostate Specific Antigen (PSA) screening, the incidence of PCa shows a linear rising trend, and most of patients have been diagnosed with advanced prostate cancer, which has become a malignant urinary tumor that seriously affects the health of men.

Abiraterone acetate is a prodrug of Abiraterone and may be transformed into Abiraterone in vivo. Currently, in clinical practice, Abiraterone acetate tablets are used. Originally developed by Johnson & Johnson, these tablets were approved by the U.S. Food and Drug Administration in 2011 for use in combination with prednisone or prednisolone in the treatment of metastatic castration-resistant prostate cancer. They have since been approved for the treatment of newly diagnosed high-risk metastatic endocrine therapy-sensitive prostate cancer. The Abiraterone acetate tablets are poor in water solubility. According to data that has been disclosed by FDA, the Abiraterone acetate tablets have low bioavailability. Pharmacokinetic experiments of animals show that the relative bioavailability of mice in vivo is 37%, whereas the relative bioavailability of monkeys and minipigs in vivo is only 1.6-1.7%. Data from clinical pharmacologic experiments in mass balance shows that 88% of drugs are excreted from faeces and 5% of drugs are excreted from urine after oral administration, based on which the bioavailability in human bodies is estimated to be lower than 10%. The absorption of the Abiraterone acetate tablets is significantly impacted by food. Therefore, it is recommended not to take food within 2 hours before administration and 1 hour after administration. Food intake may lead to a 7-fold increase and a 5-fold increase in $C_{max}$ and $AUC_{0-24}$, respectively as compared to the fasting state, and especially, the intake of high-fat meal may lead to a 17-fold increase and a 10-fold increase in $C_{max}$ and $AUC_{0-24}$, respectively. Additionally, the Abiraterone inhibits the activity of CYP17A1, leading to the secretion of excessive mineralocorticoid which results in hypokalemia, hypertension and sodium and water retention, and adverse effects, such as adrenal cortex insufficiency, hepatotoxicity, and cardiotoxicity, may also be caused by long-term clinical application. Animal studies have also found that the Abiraterone may have toxic effects which may lead to impaired reproductive or developmental function.

In response to the current issues of extremely low bioavailability, and toxic or side effects associated with the Abiraterone, the existing solution primarily focuses on changing the dosage form. For example, Abiraterone, phospholipids, and cholesterol are dissolved in organic solvents, and are then added with surfactants, such as polyethylene glycol, Tween 80, sodium carboxymethylcellulose or polysorbate, to obtain Abiraterone flexible liposomes, so that the transmembrane transport of the Abiraterone is improved, and the permeability is enhanced to improve the bioavailability of the Abiraterone; or the Abiraterone is encapsulated or bonded on biological materials, such as serum albumin, so that the water solubility is improved. Nevertheless, the improvement method of the series of preparations has a plurality of problems, such as complex preparation processes, challenges in achieving large-scale production, and failure in effectively improving the activity and reducing the toxicity of the Abiraterone. Therefore, the development of water-soluble Abiraterone compounds which are easy for industrial production and may effectively improve the effect of resisting neoplasm prostate has important academic value and social significance.

This lab has been dedicated to studies on the water-soluble compounds for an extended period of time. At the early stage, the lab developed aminopolycarboxylic acid modified taxol compounds, which improved the water solubility of taxol, docetaxel and cabazitaxel. Meanwhile, these compounds exhibit better anti-tumor activity than the precursor compounds of taxol, docetaxel and cabazitaxel. Related patents are also applied. Therefore, the injectable Abiraterone compounds with high efficiency, low toxicity and good water solubility are developed from the polyaminopolycarboxylic acid modified abiraterone derivative, which may greatly enrich drugs and approaches for treating the prostate cancer tumor.

SUMMARY

The first objective of the present disclosure is to provide an injection polyaminopolycarboxylic acid modified Abiraterone derivative to overcome defects in the prior art.

The second objective of the present disclosure is to provide a preparation method of the polyaminopolycarboxylic acid modified Abiraterone derivative.

The third objective of the present disclosure is to provide a pharmaceutic preparation, including the polyaminopolycarboxylic acid modified Abiraterone derivative as an active ingredient and an excipient, a solubiliser, a solubilizing emulsifier, and an anti-oxidant.

The fourth objective of the present disclosure is to provide the polyaminopolycarboxylic acid modified Abiraterone derivative and an application of the pharmaceutical preparation thereof as an anti-tumor drug.

The technical solutions of the present disclosure are as follows:

The injection polyaminopolycarboxylic acid modified Abiraterone derivative has the following structure:

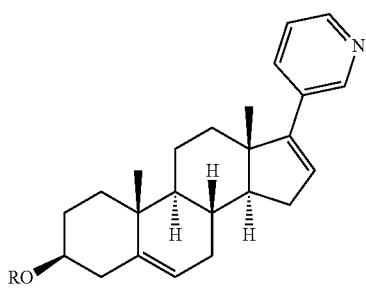

Where, R=

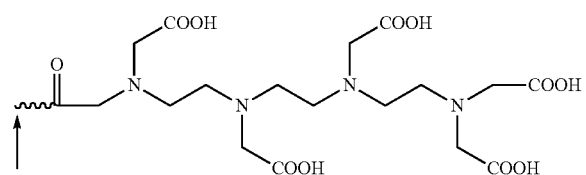

or

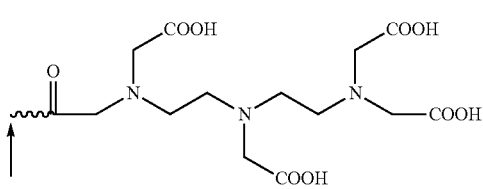

or

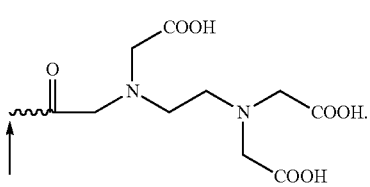

The preparation method of the polyaminopolycarboxylic acid modified Abiraterone derivative is characterized in that Abiraterone reacts with polyaminopolycarboxylic acid monoanhydride under the action of an alkaline catalyst at a ratio of 1:1.1-1:3, and the polyaminopolycarboxylic acid modified Abiraterone derivative is obtained, wherein the polyaminopolycarboxylic acid modified Abiraterone derivative has the following structure:

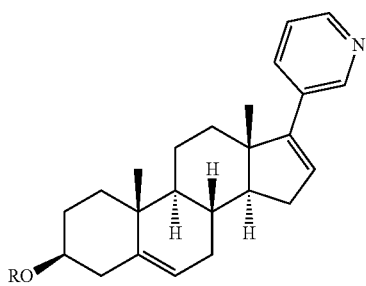

Where, R=

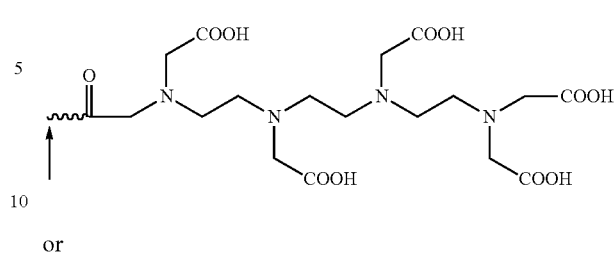

or

or

Preferably, the method includes steps of dissolving the Abiraterone and the polyaminopolycarboxylic acid monoanhydride (with molar equivalent being 1.1-3 times that of Abiraterone) in N,N-dimethylformamide or N-methyl pyrrolidone or dimethyl sulfoxide, reacting at a temperature of −10-40° C. for 5 to 48 hours under the condition of the alkaline catalyst, after reacting completely, performing suction filtration to remove an insoluble substance, adding glacial ether to a filtrate, standing at a temperature of −40° C. for more than 2 hours until a precipitate is completely separated out, collecting the precipitate via centrifugation, dissolving the precipitate in a mixed solution of water and acetonitrile, extracting with ether, collecting an aqueous phase, freeze-drying the aqueous phase, and obtaining the polyaminopolycarboxylic acid modified Abiraterone derivative.

The pharmaceutical preparation of the polyaminopolycarboxylic acid modified Abiraterone derivative, wherein an active ingredient is the polyaminopolycarboxylic acid modified Abiraterone derivative, a freeze-dried excipient is mannitol or glucose, a cosolvent is sodium bicarbonate or sodium carbonate or potassium carbonate or sodium hydroxide or potassium hydroxide, an emulsifying cosolvent is glycerin or polyethylene glycol (molecular weight of 300 or 400) or propylene glycol, and an anti-oxidant is sodium hydrogensulfite or sodium sulfite or sodium thiosulphate.

The polyaminopolycarboxylic acid modified Abiraterone derivative and an application of the pharmaceutical preparation thereof in the preparation of the anti-tumor drug.

The polyaminopolycarboxylic acid modified Abiraterone derivative of the present disclosure has high water solubility, can be dissolved completely in an aqueous solution of sodium bicarbonate, is simple and convenient to prepare, high in yield, and suitable for large-scale production, has a remarkable effect in resisting tumors, can be used for treating prostate cancer tumor, and has the characteristics of high efficiency and low toxicity.

DETAILED DESCRIPTION OF THE EMBODIMENTS

Figure 1:
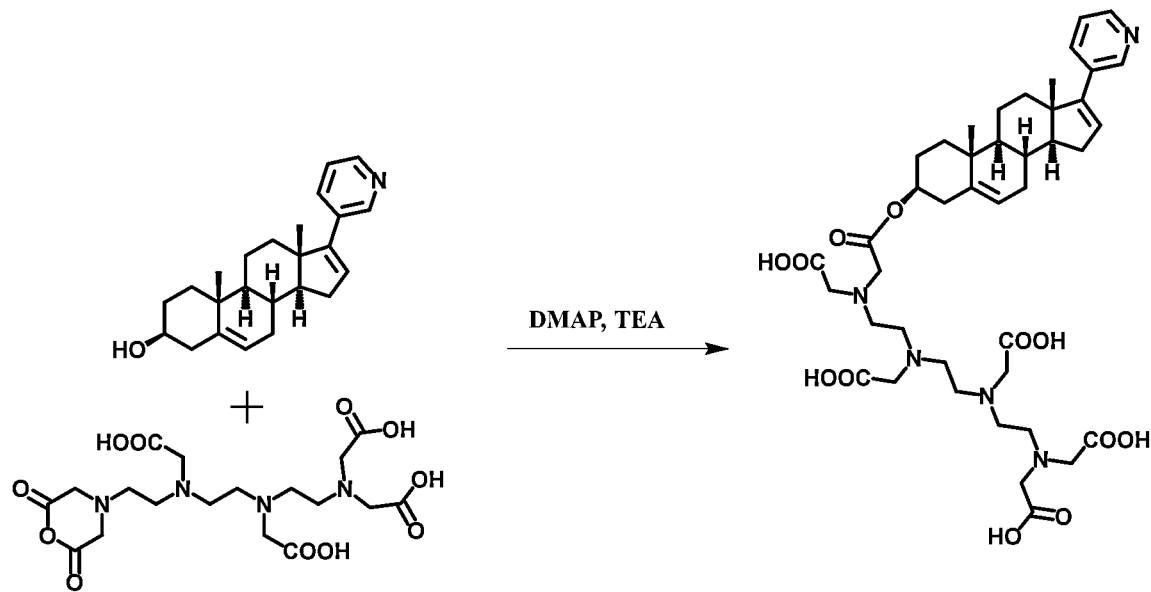
FIG. 1 is a synthetic route of a triethylenetetramine hexaacetic acid modified Abiraterone derivative AA-TTHA of Example 1 according to the present disclosure.

The present disclosure will be further illustrated by the following examples, which are intended only for a better understanding of the present disclosure, but do not limit the scope of protection of the present disclosure:

Example 1 Synthesis of Triethylenetetramine Hexaacetic Acid Modified Abiraterone Derivative AA-TTHA 1 mmol of Abiraterone and 3 mmol of triethylenetetramine hexaacetic acid monoanhydride are dissolved in 30 ml of N,N-dimethylformamide, 1.5 mmol of N-dimethylaminopyridine and 3 mmol of triethylamine are then added, and a mixture reacts at 40° C. for 5 hours with stirring. After a reaction is finished, insoluble substances are removed from a system by suction filtration, a filtrate is precipitated with 200 ml of glacial ether, a mixture is placed at −40° C. overnight, and solid precipitates are collected by centrifugation after being separated out completely. The precipitates are dissolved completely in water and acetonitrile, and extracted with ether, an aqueous phase is collected and freeze-dried, and 0.79 g of triethylenetetramine hexaacetic acid modified Abiraterone derivative AA-TTHA is obtained, with a yield of 72.1% (a synthesis route is shown in FIG. 1).

Figure 2:
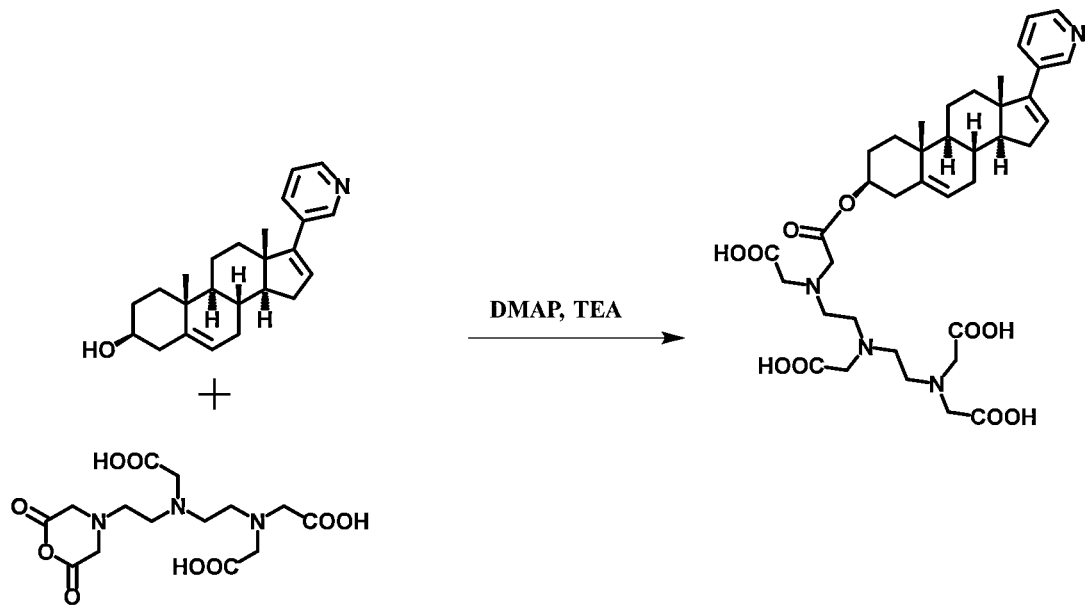
FIG. 2 is a synthetic route of a diethylenetriaminepentaacetic acid modified Abiraterone derivative AA-DTPA of Example 2 according to the present disclosure.
Figure 3:
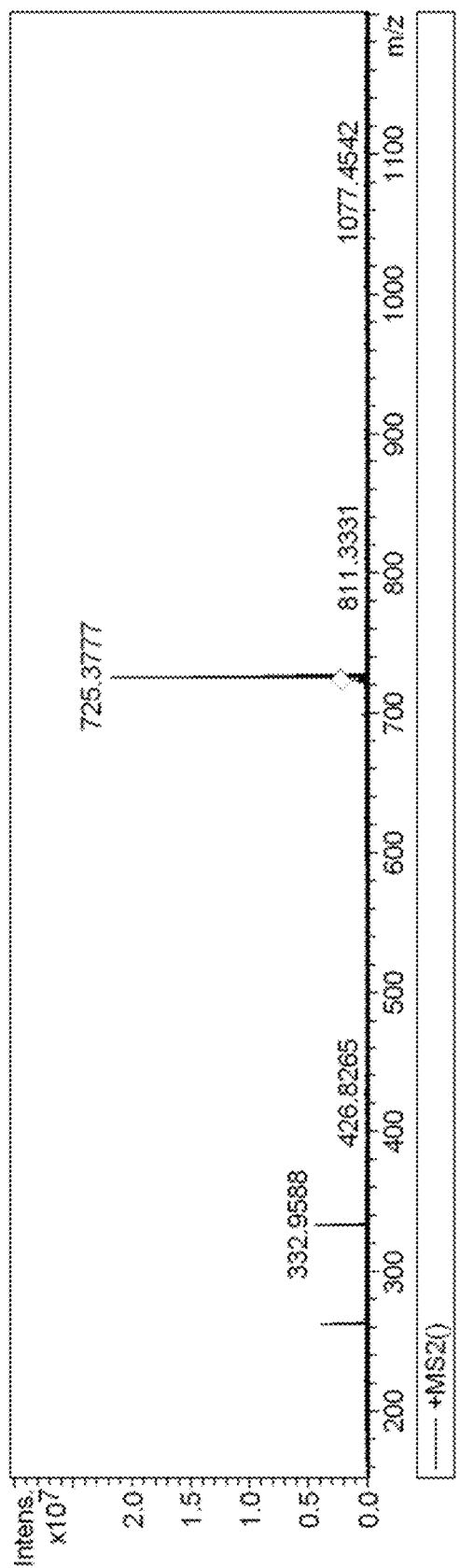
FIG. 3 is a high-resolution mass spectrum of a diethylenetriaminepentaacetic acid modified Abiraterone derivative AA-DTPA of Example 2 according to the present disclosure.
Figure 4:
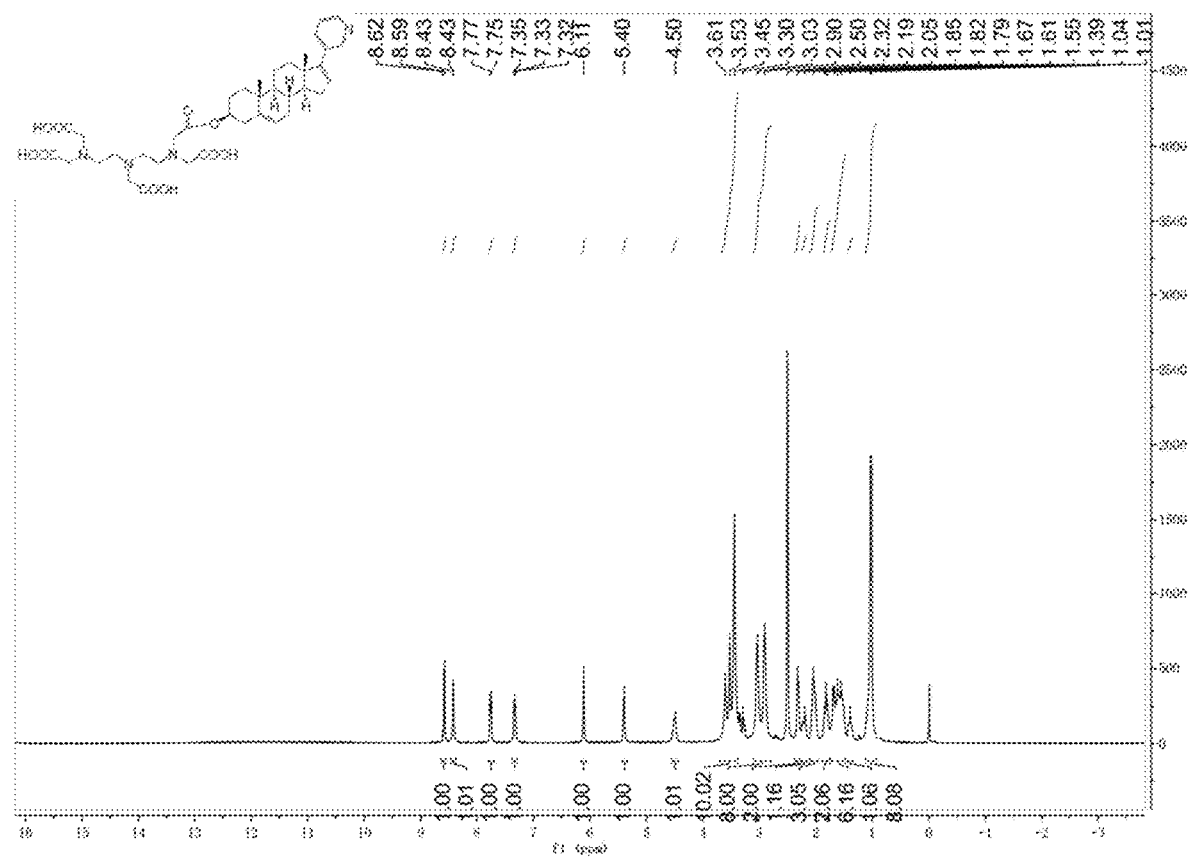
FIG. 4 is a nuclear magnetic resonance hydrogen spectrum of a diethylenetriaminepentaacetic acid modified Abiraterone derivative AA-DTPA of Example 2 according to the present disclosure.

Example 2 Synthesis of Diethylenetriaminepentaacetic Acid Modified Abiraterone Derivative AA-DTPA 1 mmol of Abiraterone and 2 mmol of diethylenetriaminepentaacetic acid monoanhydride are dissolved in 30 ml of N-methyl pyrrolidone, 1.5 mmol of N-dimethylaminopyridine and 2 mmol of triethylamine are then added, and a mixture reacts at −10° C. for 48 hours with stirring. After a reaction is finished, insoluble substances are removed from a system by suction filtration, a filtrate is precipitated with 300 ml of glacial ether, a mixture is placed at −40° C. overnight, and solid precipitates are collected by centrifugation after being separated out completely. The precipitates are dissolved completely in water and acetonitrile, and extracted with ether, an aqueous phase is collected and freeze-dried, and 1.13 g of diethylenetriaminepentaacetic acid modified Abiraterone derivative AA-DTPA is obtained, with a yield of 87.5%. (A synthesis route is shown in FIG. 2, a high-resolution mass spectrum is shown in FIG. 3, and a nuclear magnetic resonance hydrogen spectrum is shown in FIG. 4).

Figure 5:
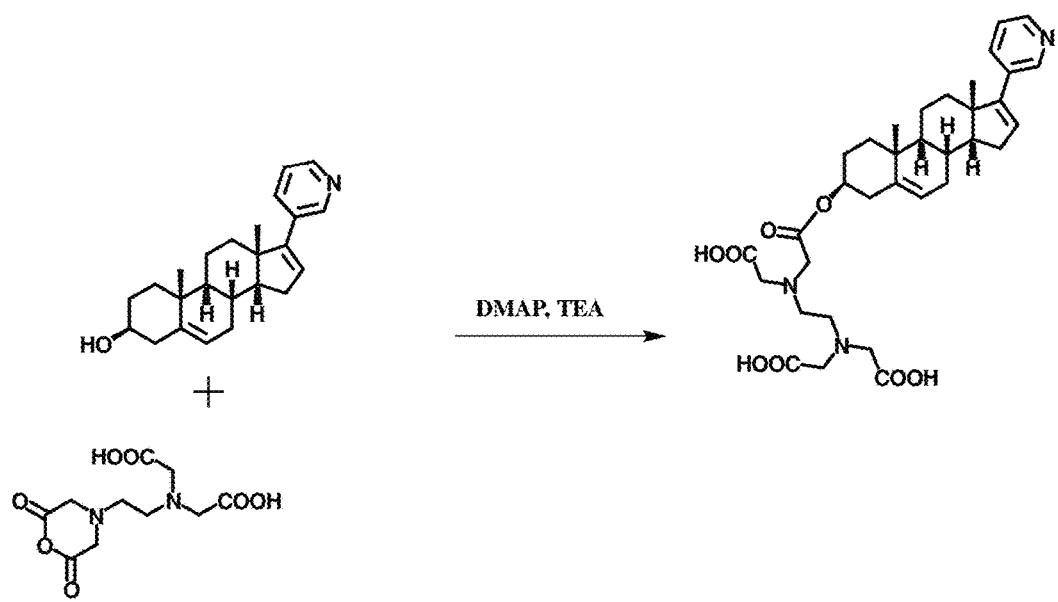
FIG. 5 is a synthetic route of an ethylenediamine tetra-acetic acid modified Abiraterone derivative AA-EDTA of Example 3 according to the present disclosure.
Figure 6:
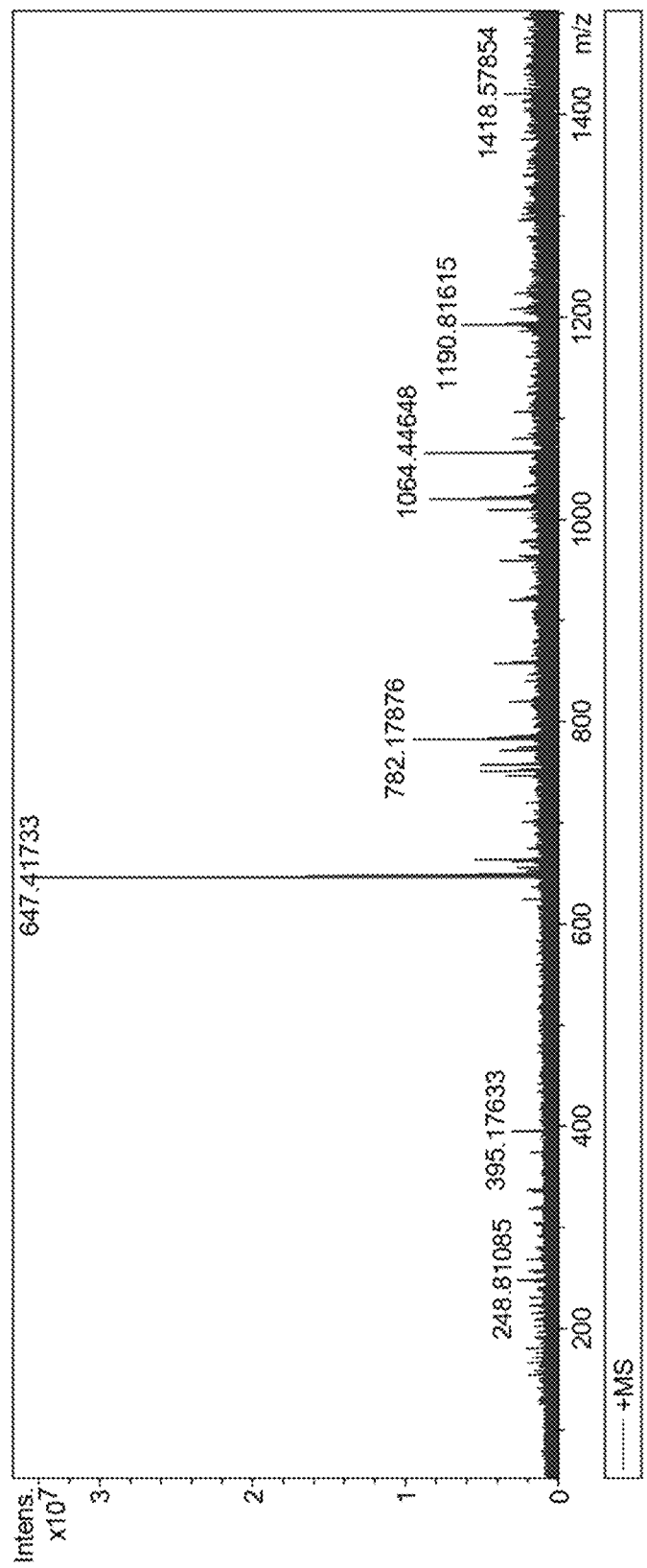
FIG. 6 is a high-resolution mass spectrum of an ethylenediamine tetra-acetic acid modified Abiraterone derivative AA-EDTA of Example 3 according to the present disclosure.

Example 3 Synthesis of Ethylenediamine Tetra-Acetic Acid Modified Abiraterone Derivative AA-EDTA 1 mmol of Abiraterone and 1.5 mmol of ethylenediamine tetra-acetic acid monoanhydride are dissolved in 30 ml of dimethyl sulfoxide, 1 mmol of N-dimethylaminopyridine and 1.5 mmol of triethylamine are then added, and a mixture reacts at 25° C. for 24 hours with stirring. After a reaction is finished, insoluble substances are removed from a system by suction filtration, a filtrate is precipitated with 300 ml of glacial ether, a mixture is placed at −40° C. overnight, and solid precipitates are collected by centrifugation after being separated out completely. The precipitates are dissolved completely in water and acetonitrile, and extracted with ether, an aqueous phase is collected and freeze-dried, and 0.91 g of ethylenediamine tetra-acetic acid modified Abiraterone derivative AA-EDTA is obtained, with a yield of 75.6% (a synthesis route is shown in FIG. 5, and a high-resolution mass spectrum is shown in FIG. 6).

Example 4 Synthesis of Triethylenetetramine Hexaacetic Acid Modified Abiraterone Derivative AA-TTHA 3 mmol of Abiraterone and 6 mmol of triethylenetetramine hexaacetic acid monoanhydride are dissolved in 60 ml of dimethyl sulfoxide, 3 mmol of N-dimethylaminopyridine and 6 mmol of triethylamine are then added, and a mixture reacts at 40° C. for 10 hours with stirring. After a reaction is finished, insoluble substances are removed from a system by suction filtration, a filtrate is precipitated with 400 ml of glacial ether, a mixture is placed at −40° C. for 6 hours, and solid precipitates are collected by centrifugation after being separated out completely. The precipitates are dissolved completely in water and acetonitrile, and extracted with ether, an aqueous phase is collected and freeze-dried, and 2.16 g of triethylenetetramine hexaacetic acid modified Abiraterone derivative AA-TTHA is obtained, with a yield of 87.2%.

Example 5 Synthesis of Diethylenetriaminepentaacetic Acid Modified Abiraterone Derivative AA-DTPA 3 mmol of Abiraterone and 9 mmol of diethylenetriaminepentaacetic acid monoanhydride are dissolved in 100 ml of N,N-dimethylformamide, 4 mmol of N-dimethylaminopyridine and 9 mmol of triethylamine are then added, and a mixture reacts at 25° C. for 36 hours with stirring. After a reaction is finished, insoluble substances are removed from a system by suction filtration, a filtrate is precipitated with 500 ml of glacial ether, a mixture is placed at −40° C. for 4 hours, and solid precipitates are collected by centrifugation after being separated out completely. The precipitates are dissolved completely in water and acetonitrile, and extracted with ether, an aqueous phase is collected and freeze-dried, and 1.87 g of diethylenetriaminepentaacetic acid modified Abiraterone derivative AA-DTPA is obtained, with a yield of 86.1%.

Example 6 Synthesis of Ethylenediamine Tetra-Acetic Acid Modified Abiraterone Derivative AA-EDTA 3 mmol of Abiraterone and 7.5 mmol of ethylenediamine tetra-acetic acid monoanhydride are dissolved in 60 ml of N-dimethylaminopyridine, 3 mmol of N-dimethylaminopyridine and 7.5 mmol of triethylamine are then added, and a mixture reacts at 10° C. for 48 hours with stirring. After a reaction is finished, insoluble substances are removed from a system by suction filtration, a filtrate is precipitated with 400 ml of glacial ether, a mixture is placed at −40° C. for 2 hours, and solid precipitates are collected by centrifugation after being separated out completely. The precipitates are dissolved completely in water and acetonitrile, and extracted with ether, an aqueous phase is collected and freeze-dried, and 1.64 g of ethylenediamine tetra-acetic acid modified Abiraterone derivative AA-EDTA is obtained, with a yield of 87.7%.

Example 7 Preparation of AA-TTHA Freeze-Dried Powder for Injection 0.2 g of AA-TTHA prepared in Example 1, 6 g of mannitol, and 0.01 g of sodium hydrogensulfite are taken and dissolved in 40 ml of water for injection, 1 g of medicinal activated carbon is then added, a mixture is stirred at a room temperature for 20 minutes, the activated carbon is filtered out, the mixture is then sterilized by filtration through a 0.22 μm filter membrane, and the mixture is subpackaged into 5 ml vials (each with 2 ml), and freeze-dried.

Example 8 Preparation of AA-TTHA Freeze-Dried Powder for Injection 2.0 g of AA-TTHA prepared in Example 4, 20 g of glucose, 0.4 g of sodium bicarbonate, and 0.03 g of sodium sulfite are taken and dissolved in 100 ml of water for injection, 10 g of medicinal activated carbon is then added, a mixture is stirred at a room temperature for 20 minutes, the activated carbon is filtered out, the mixture is then sterilized by filtration through a 0.22 μm filter membrane, and the mixture is subpackaged into 10 ml vials (each with 5 ml), and freeze-dried.

Example 9 Preparation of AA-DTPA Freeze-Dried Powder for Injection 0.2 g of AA-DTPA prepared in Example 2, 8 g of glucose, 0.2 ml of glycerol, and 0.01 g of sodium sulfite are taken and dissolved in 80 ml of water for injection, 1 g of medicinal activated carbon is then added, a mixture is stirred at a room temperature for 20 minutes, the activated carbon is filtered out, the mixture is then sterilized by filtration through a 0.22 μm filter membrane, and the mixture is subpackaged into 5 ml vials (each with 2 ml), and freeze-dried.

Example 10 Preparation of AA-DTPA Freeze-Dried Powder for Injection 2.0 g of AA-DTPA prepared in Example 5, 30 g of mannitol, 0.6 g of sodium carbonate, and 0.05 g of sodium sulfite are taken and dissolved in 200 ml of water for injection, 10 g of medicinal activated carbon is then added, a mixture is stirred at a room temperature for 20 minutes, the activated carbon is filtered out, the mixture is then sterilized by filtration through a 0.22 μm filter membrane, and the mixture is subpackaged into 10 ml vials (each with 5 ml), and freeze-dried.

Example 11 Preparation of AA-EDTA Freeze-Dried Powder for Injection 0.2 g of AA-EDTA prepared in Example 3, 8 g of mannitol, 0.5 ml of polyethylene glycol (molecular weight of 300), and 0.01 g of sodium thiosulphate are taken and dissolved in 40 ml of water for injection, 1 g of medicinal activated carbon is then added, a mixture is stirred at a room temperature for 20 minutes, the activated carbon is filtered out, the mixture is then sterilized by filtration through a 0.22

μm filter membrane, and the mixture is subpackaged into 5 ml vials (each with 2 ml), and freeze-dried.

Example 12 Preparation of AA-EDTA Freeze-Dried Powder for Injection 2.0 g of AA-EDTA prepared in Example 6, 30 g of glucose, 0.45 g of potassium carbonate, and 0.01 g of sodium sulfite are taken and dissolved in 200 ml of water for injection, 10 g of medicinal activated carbon is then added, a mixture is stirred at a room temperature for 20 minutes, the activated carbon is filtered out, the mixture is then sterilized by filtration through a 0.22 μm filter membrane, and the mixture is subpackaged into 10 ml vials (each with 5 ml), and freeze-dried.

Example 13 In Vitro Anti-Tumor Effect (LNCaP) of Polyaminopolycarboxylic Acid Modified Abiraterone Derivative In vitro anti-tumor evaluation of the AA-EDTA, the AA-DTPA, and the AA-TTHA prepared in Examples 1-6 on human prostate cancer cells (LNCaP) includes the following steps:

The human prostate cancer cells (LNCaP) in an exponential phase of growth were taken, after being digested with trypsin, the human prostate cancer cells were re-suspended in an RPMI 1640 culture medium containing 15% fetal bovine serum, and inoculated into a 96-well plate at a density of $1 \times 10^4$ cells/well, and the 96-well plate was then placed in a cell incubator for culture for 24 hours.

The culture medium was discarded, and 100 μl of drug solutions was added to each well at different concentrations being 2.5 μM, 5 μM, 10 μM, 20 μM, 40 μM, 80 μM, and 160 μM sequentially; and 5 replicate wells were set up for each concentration, and placed in the incubator for incubation for 48 hours.

Cell survival rate tested by CCK8 method: after the solution was pipetted from the wells, each well was added with 10 μl of CCK8 reagent and 100 μl of serum-free medium for further culture for 4 hours. An absorbance value of each well at 450 nm was determined using a microplate reader. The cell survival rate was calculated with cells cultured without incubation by compounds as a blank control, with results as shown in FIG. 7.

Figure 7:
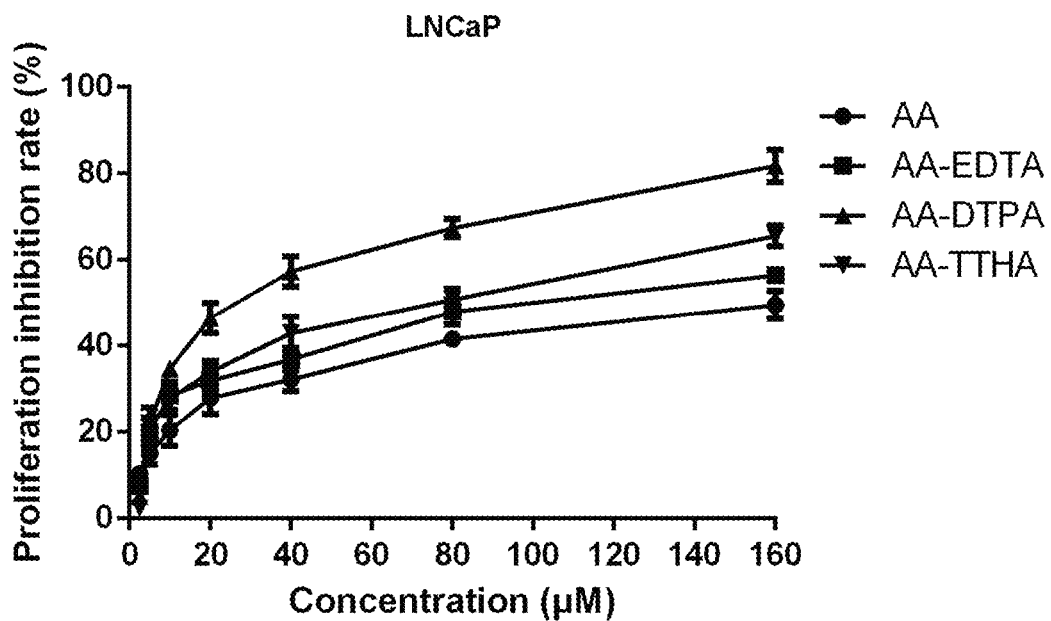
FIG. 7 shows an anti-tumor effect of a polyaminopolycarboxylic acid modified Abiraterone derivative on human prostate cancer cells (LNCaP) in Example 13 according to the present disclosure.

As can be seen from FIG. 7, the in vitro anti-tumor effects (LNCaP) of the polyaminopolycarboxylic acid modified Abiraterone derivatives AA-EDTA, AA-DTPA, and AA-TTHA were superior to the in vitro anti-tumor effect of Abiraterone AA.

Example 14 In Vitro Anti-Tumor Effect (DU145) of Polyaminopolycarboxylic Acid Modified Abiraterone Derivative In vitro anti-tumor evaluation of the AA-EDTA, the AA-DTPA, and the AA-TTHA prepared in Examples 1-6 on human prostate cancer cells (DU145) includes the following steps:

The human prostate cancer cells (DU145) in an exponential phase of growth were taken, after being digested with trypsin, the human prostate cancer cells were re-suspended in an RPMI 1640 culture medium containing 15% fetal bovine serum, and inoculated into a 96-well plate at a density of $4 \times 10^3$ cells/well, and the 96-well plate was then placed in a cell incubator for culture for 24 hours.

The culture medium was discarded, and 100 μl of drug solutions was added to each well at different concentrations being 2.5 μM, 5 μM, 10 μM, 20 μM, 40 μM, 80 μM, and 160 μM sequentially; and 5 replicate wells were set up for each concentration, and placed in the incubator for incubation for 48 hours.

Cell survival rate tested by CCK8 method: after the solution was pipetted from the wells, each well was added with 10 μl of CCK8 reagent and 100 μl of serum-free medium for further culture for 4 hours. An absorbance value of each well at 450 nm was determined using a microplate reader. The cell survival rate was calculated with cells cultured without incubation by compounds as a blank control, with results as shown in FIG. 8.

Figure 8:
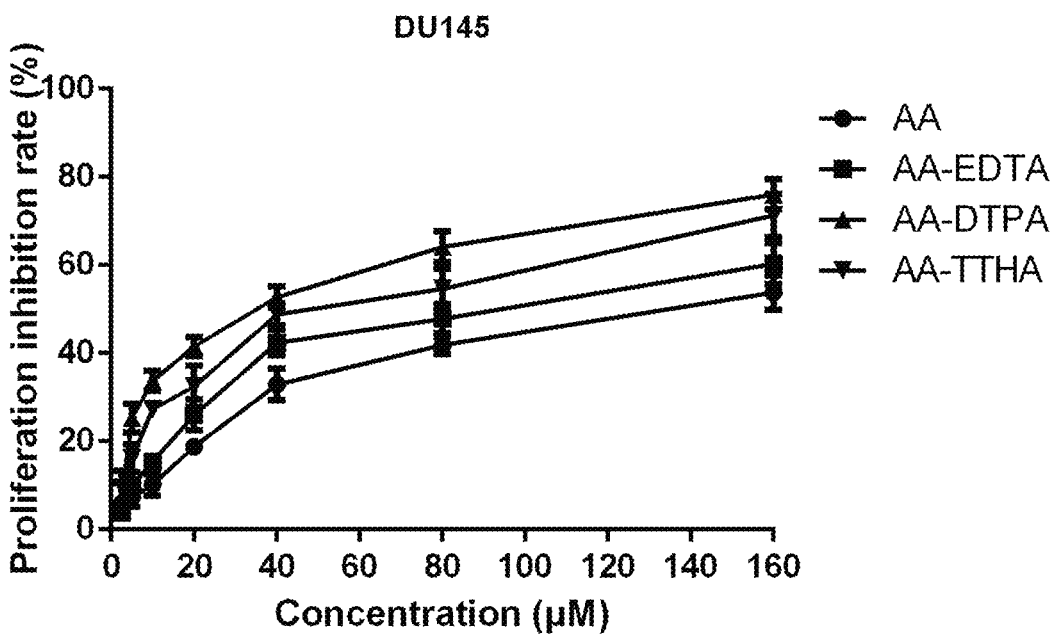
FIG. 8 shows an anti-tumor effect of a polyaminopolycarboxylic acid modified Abiraterone derivative on human prostate cancer cells (DU145) in Example 14 according to the present disclosure.

As can be seen from FIG. 8, the in vitro anti-tumor effects (DU145) of the polyaminopolycarboxylic acid modified Abiraterone derivatives AA-EDTA, AA-DTPA, and AA-TTHA were superior to the in vitro anti-tumor effect of Abiraterone AA.

Example 15 Inhibition of Growth of Human Prostate Cancer LNCaP Derived Xenograft Tumors of Nude Mice by Polyaminopolycarboxylic Acid Modified Abiraterone Derivative The in vivo experimental process of AA-DTPA prepared in Example 2 in treatment of transplanted prostate cancer LNCaP tumor-bearing mice includes the following steps:

A human prostate cancer cell line (LNCaP) in an exponential phase of growth was taken, and prepared into a cell suspension containing $5 \times 10^7$ cells/ml under an aseptic condition, 0.1 ml of cell suspension was inoculated into a right armpit of each nude mouse subcutaneously, and the mice were then randomized into groups after tumors grew to 100 to 200 mm$^3$.

A normal group (Normal) was not given any treatment; a model group (NS) received a daily injection of an equal volume of physiological saline; an AA group (150 mg/kg/d p.o.) was administrated intragastrically, once daily; and an AA-DTPA group (35 mg/kg/w i.v.) and an AA-DTPA group (52.5 mg/kg/w i.v.) were administrated from tail veins once weekly. After treatment for 28 days, the mice were sacrificed and the tumor mass was surgically removed and weighed, and results were shown in FIG. 9.

Diameters of the xenograft tumors of the nude mice were measured with vernier calipers, and the anti-tumor effect of the Abiraterone was dynamically observed. Measurement of body weight and tumor size of each mouse: tumor diameter was measured twice per week, the length and width of the tumor were measured, and a body weight gain curve and a tumor growth curve of the mice were plotted according to a formula: tumor volume (mm$^3$)=½×length×width$^2$. Results were shown in FIGS. 10-11.

Two days following the last administration, the mice were sacrificed, and hearts, livers, spleens, lungs, kidneys, and testes were dissected off and weighed, and organ indexes [organ index=organ weight/(body weight−tumor weight), unit: mg/g] were calculated. Results from organ index experiments were shown in FIG. 12.

Figure 9:
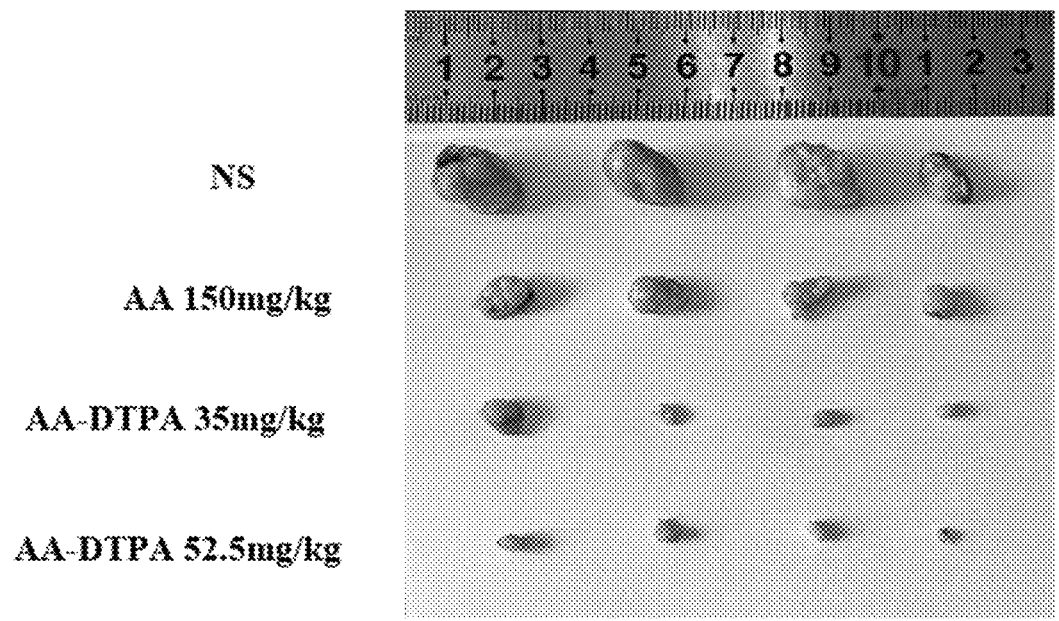
FIG. 9 is a photograph showing experimental results of an in vivo anti-tumor effect of a polyaminopolycarboxylic acid modified Abiraterone derivative on prostate cancer LNCaP tumor-bearing mice in Example 15 according to the present disclosure.
Figure 11:
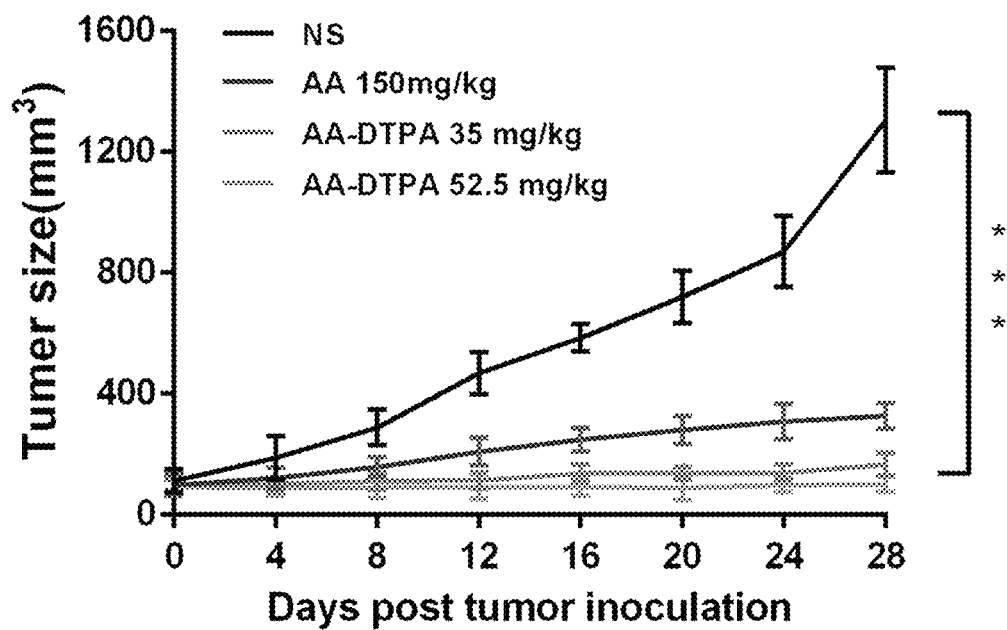
FIG. 11 is a chart showing experimental results of an in vivo anti-tumor effect of a polyaminopolycarboxylic acid modified Abiraterone derivative on prostate cancer LNCaP tumor-bearing mice in Example 15 according to the present disclosure.

As can be seen from FIGS. 9 and 11, after contrast treatment for 28 days, the tumor growth was significantly inhibited in the AA group, as well as in the AA-DTPA group (35 mg/kg/w) and the AA-DTPA group (52.5 mg/kg/w) of the polyaminopolycarboxylic acid modified Abiraterone derivative under the same conditions, and the AA-DTPA group (35 mg/kg/w) and the AA-DTPA group (52.5 mg/kg/ w) had better tumor inhibition effects, compared with the tumor inhibition effect of the AA group.

Figure 12:
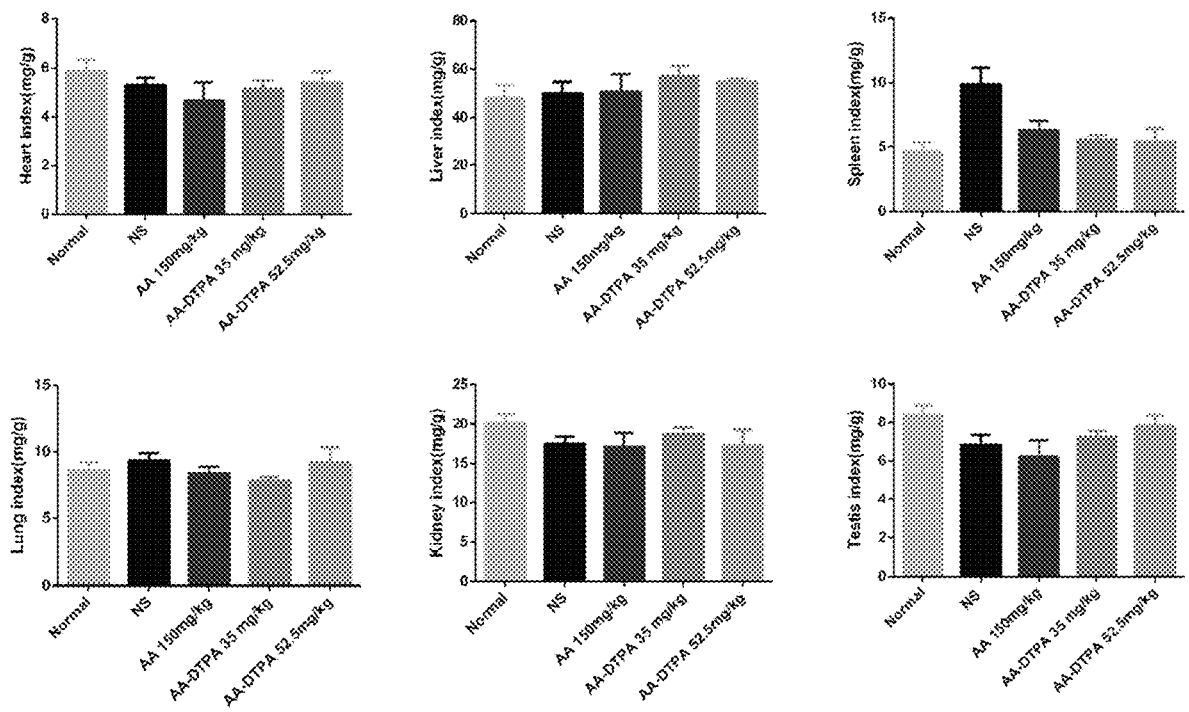
FIG. 12 is a chart showing experimental results of an effect of a polyaminopolycarboxylic acid modified Abiraterone derivative on organ indexes of prostate cancer LNCaP tumor-bearing mice in Example 15 according to the present disclosure.

As can be seen from FIG. 12, after the contrast treatment for 28 days, spleen indexes were significantly increased in the model group under the same conditions, and the spleens were enlarged, indicating a decrease in body immunity in the mice of the model group. Compared with the normal group and the model group, testicular atrophy and a sharp decrease in testis indexes were found in the mice of the AA group, indicating that AA drugs had reproductive toxicity. Additionally, a slight decline in heart indexes was also found in the mice of the AA group, and no significant difference in other indexes of organs, such as the livers, the lungs, and the kidneys, between the AA group and the model group was found. No significant difference in other indexes of the organs, such as the hearts, the livers, the lungs, the kidneys, and the testes in the AA-DTPA treatment group was found compared to the model group, indicating that the organ toxicity of the AA-DTPA was lower than that of the AA under the treatment dose.

Figure 10:
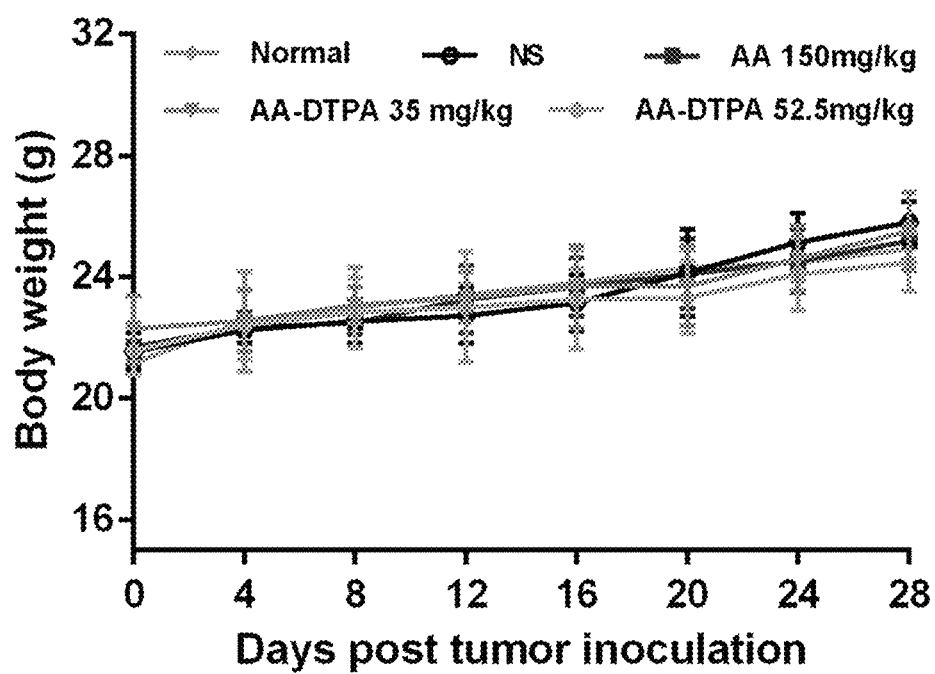
FIG. 10 is a chart showing experimental results of an effect of a polyaminopolycarboxylic acid modified Abiraterone derivative on body weights of prostate cancer LNCaP tumor-bearing mice in Example 15 according to the present disclosure.

As can be seen from FIG. 10, after the contrast treatment for 28 days, the body weights of the mice in the AA-DTPA (35 mg/kg) group and the AA-DTPA (52.5 mg/kg) group of the polyaminopolycarboxylic acid modified abiraterone derivative were equivalent to those of the mice in the normal group under the same conditions, indicating that there was no significant influence on the growth of the mice.

Example 16 Toxicity Studies of Polyaminopolycarboxylic Acid Modified Abiraterone Derivative The influence of the polyaminopolycarboxylic acid modified Abiraterone derivative AA-DTPA prepared in Example 5 on blood routine, blood biochemistry and pathological tissues of ICR healthy male mice following administration for 28 days includes the following steps:

20 ICR mice were selected, and were divided into 4 groups (NS group, positive control group AA 150 mg/kg/d p.o., and experimental groups AA-DTPA 35 mg/kg/w and 52.5 mg/kg/w i.v.), each of which had 5 mice.

Figure 13:
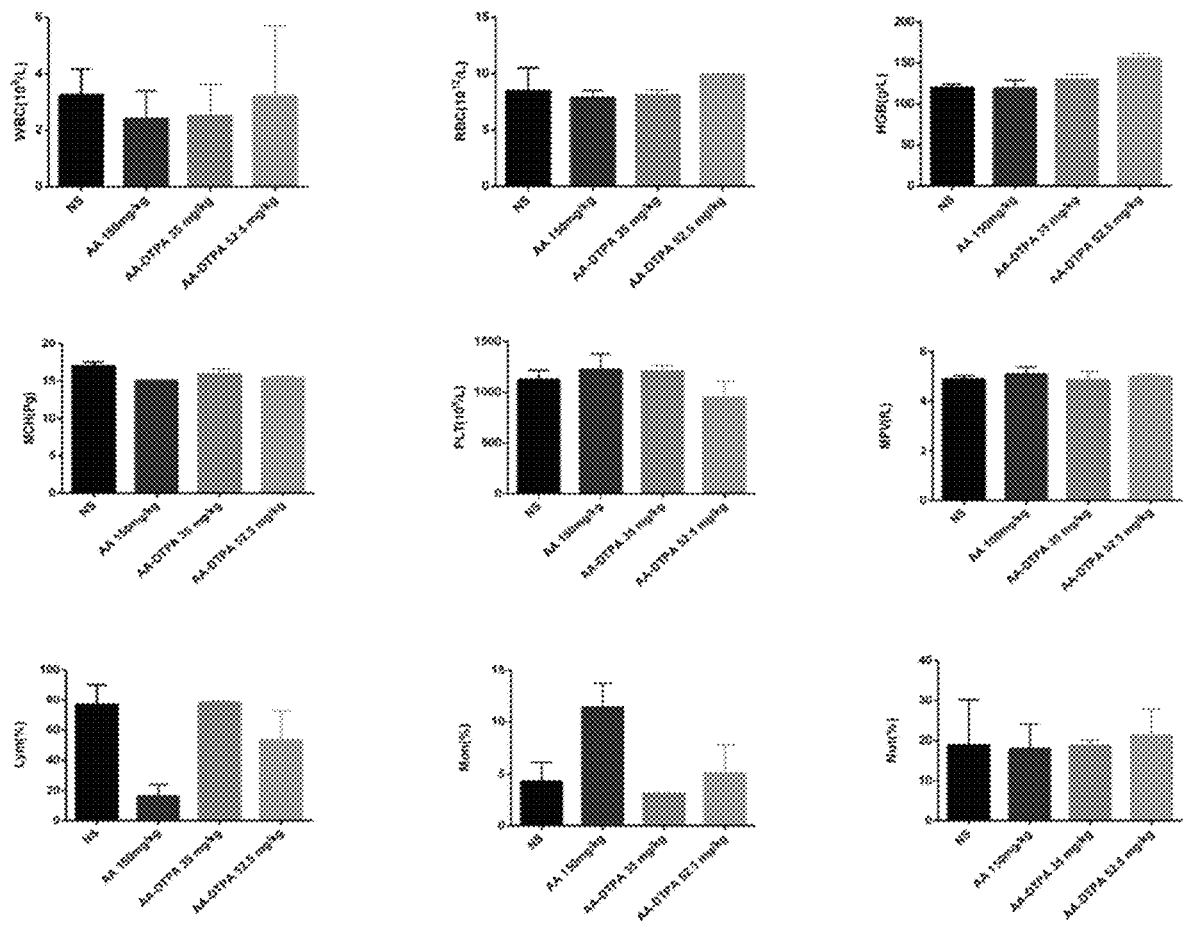
FIG. 13 is a chart showing experimental results of an effect of a polyaminopolycarboxylic acid modified Abiraterone derivative on blood routine of healthy ICR male mice in Example 16 according to the present disclosure.
Figure 14:
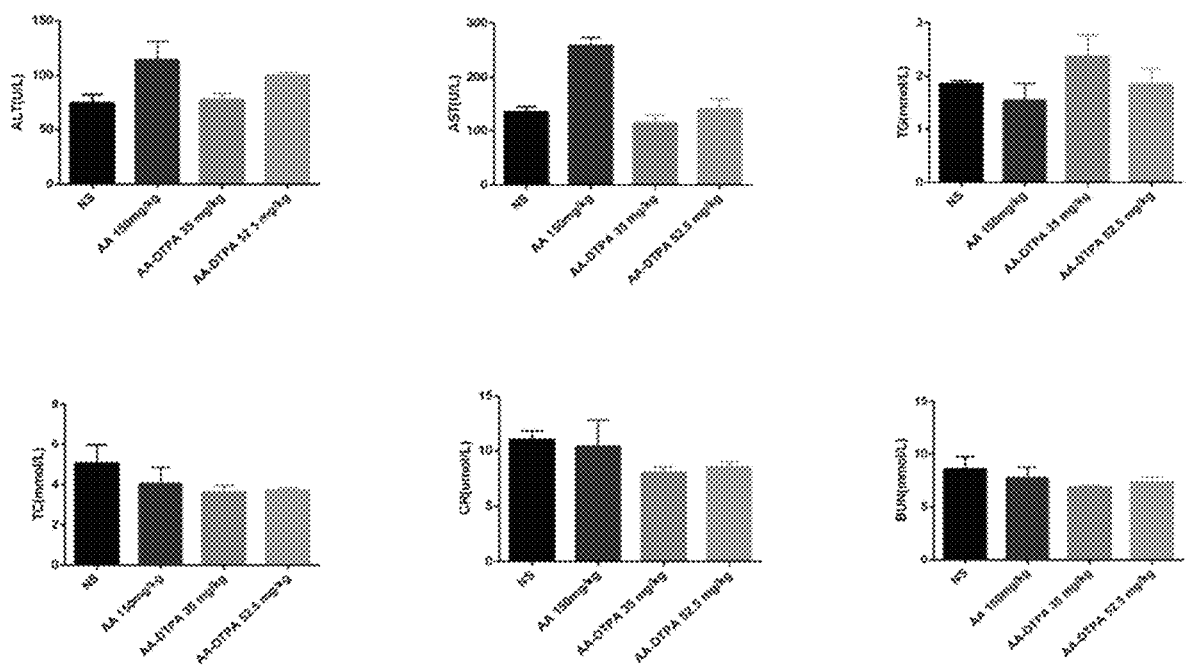
FIG. 14 is a chart showing experimental results of an effect of a polyaminopolycarboxylic acid modified Abiraterone derivative on blood biochemistry of healthy ICR male mice in Example 16 according to the present disclosure.
Figure 15:
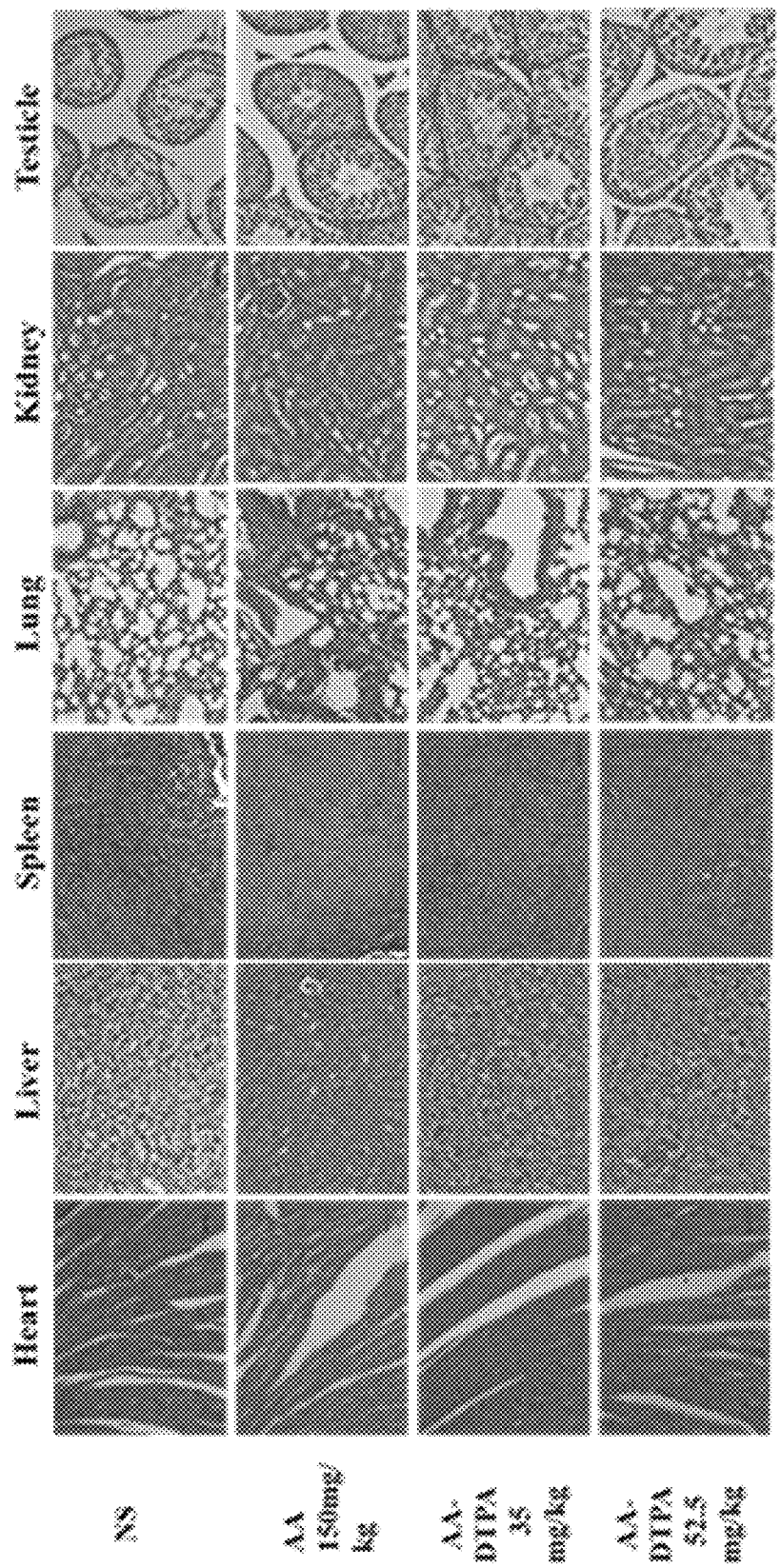
FIG. 15 is a chart showing experimental results of an effect of a polyaminopolycarboxylic acid modified Abiraterone derivative on tissue pathology of healthy ICR male mice in Example 16 according to the present disclosure.

The mice were administrated intragastrically once daily, and administrated intravenously, 1 day apart, and blood was sampled for submission following the treatment for 28 days; all mice were sacrificed by cervical dislocation, hearts, livers, spleens, lungs, kidneys, and testes were dissected and collected, and fixed with 10% formaldehyde; and after being embedded by paraffin, the organs were sectioned, and histopathological examination was performed after HE staining (see FIG. 13 for results from blood routine experiments, FIG. 14 for results from blood biochemistry experiments, and FIG. 15 for results from histopathological experiments).

As can be seen from FIG. 13, the polyaminopolycarboxylic acid modified abiraterone derivative AA-DTPA had less effect on the blood routine of the healthy male ICR mice; and the AA-DTPA had less effect on the number of lymphocytes and monocytes in the healthy male ICR mice, compared with that of the Abiraterone AA group, indicating that the AA-DTPA was less toxic than that of the AA.

As can be seen from FIG. 14, the polyaminopolycarboxylic acid modified abiraterone derivative AA-DTPA had less effect on the blood biochemistry of the healthy male ICR mice; and the AA-DTPA had less effect on alanine aminotransferase and aspartate aminotransferase in the healthy male ICR mice, compared with such effect of the Abiraterone AA group, indicating that the AA-DTPA was less toxic than that of the AA.

As can be seen from FIG. 15, the pathological section microscopic examination results showed that no abnormal changes in the hearts, the spleens, the kidneys and the testes were found, mild pathological changes were found in the lungs of the positive control group AA and the experimental group AA-DTPA 52.5 mg/kg/w, and mild pathological changes were found in the livers of the AA group, indicating that the AA-DTPA had no obvious organ toxicity and was less toxic than that of the AA.

Example 17 Pharmacokinetic Studies of Polyaminopolycarboxylic Acid Modified Abiraterone Derivative in Rats Pharmacokinetics experiments of the polyaminopolycarboxylic acid modified abiraterone derivative AA-DTPA prepared in Example 2 in rats includes the following steps:

A total of eight healthy male SD rats weighing 220+/−20 g were randomly divided into 2 groups, with 4 rats in each group; one group was administered with AA-DTPA from tail veins of the rats at a dose of 8 mg/kg in a volume of 0.2 ml/200 g rat; the other group was administrated intragastrically with AA at a dose of 30 mg/kg in a volume of 0.2 ml/200 g rat; blood samples were collected at time points of 5, 15, and 30 minutes, as well as 1, 2, 4, 6, 12, and 24 hours before and after administration for both groups; and at each time point, 0.5 ml of blood was sampled from canthi, and was placed in a heparinized plastic centrifuge tube, centrifugation was performed at 3000 r/min for 10 minutes, and plasma was separated therefrom.

50 µl of rat plasma samples+5 µl of methanol ice (1:1, v/v)+150 µl of precipitant were taken, and fully whirled and shaken for 3 minutes, a mixture was then centrifuged at 4° and 12000 r/min for 10 minutes, and a supernatant was pipetted, and analyzed with sample injection by LC-MS/MS (liquid chromatography-tandem mass spectrometry). Experimental results were shown in FIG. 16.

Figure 16:
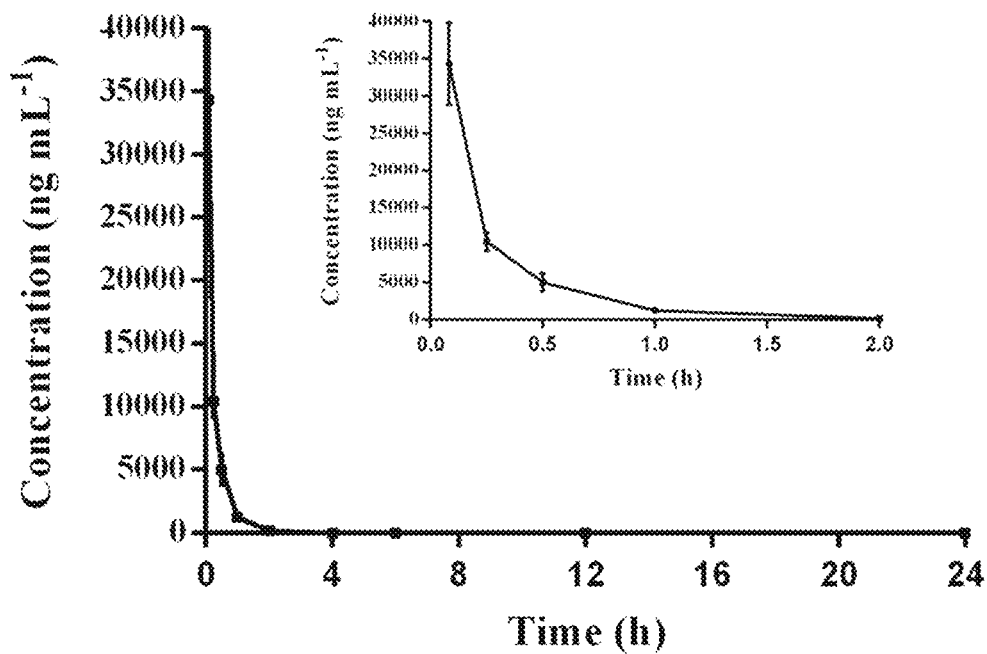
FIG. 16 is a curve chart of plasma drug concentration versus time for a polyaminopolycarboxylic acid modified Abiraterone derivative of Example 17 according to the present disclosure in rats.
Figure 17:
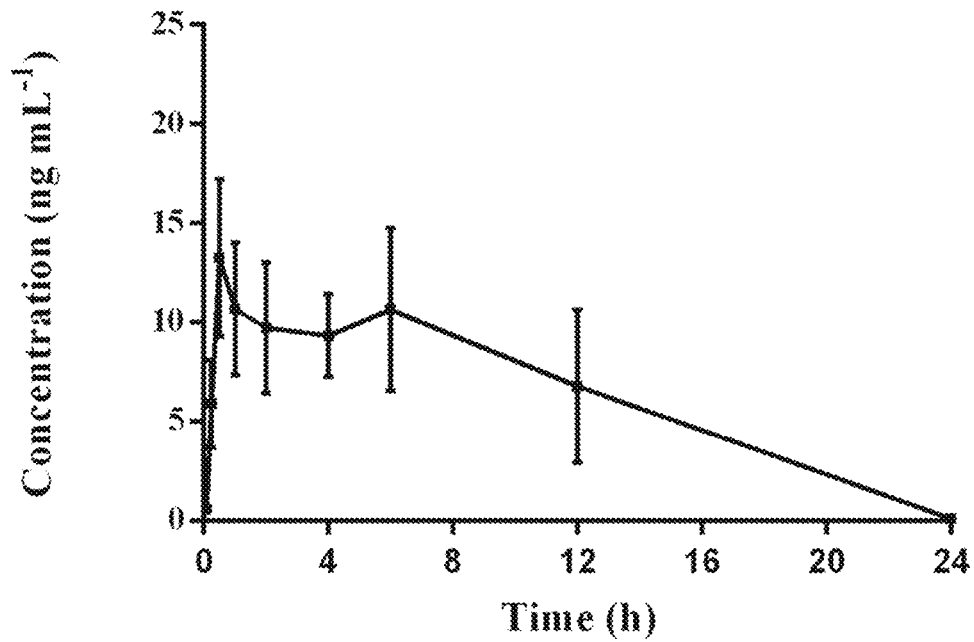
FIG. 17 is a curve chart of plasma drug concentration versus time for Abiraterone of Example 17 according to the present disclosure in rats.

As can be seen from FIG. 16, double exponential decay was shown following the intravenous injection of the AA-DTPA, the half-life period was 0.26 hour, and the average clearance rate was 0.513 L/h/kg; and the AA concentration in blood plasma reached the peak value (15.28+/−1.24 ng/ml) following intragastric administration of AA for 0.5 hour, the half-life period was 8.46 hours, the drug was absorbed slowly in vivo, and the difference in individual absorptions was large. Meanwhile, the bioavailability of the AA-DTPA was far higher than that of the AA.

What is claimed is:

1. A polyaminopolycarboxylic acid modified Abiraterone derivative, having the following structure:

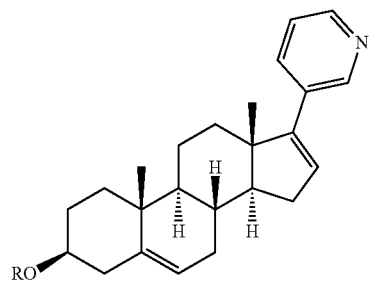

where, R=

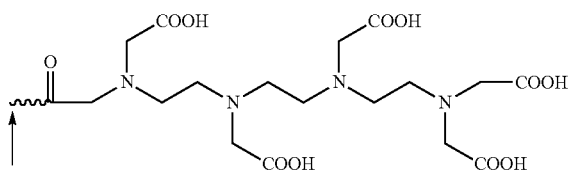

or

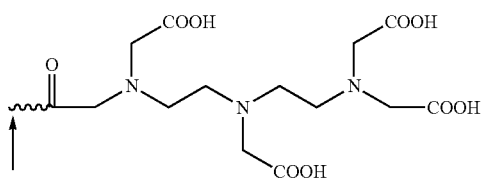

or

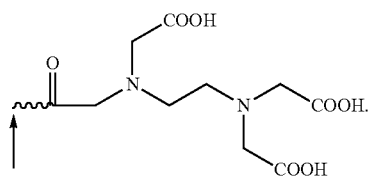

2. A method of preparing the polyaminopolycarboxylic acid modified Abiraterone derivative according to claim 1, comprising reacting Abiraterone with polyaminopolycarboxylic acid monoanhydride under an action of an alkaline catalyst at a ratio of 1:1.1-1:3, and the polyaminopolycarboxylic acid modified Abiraterone derivative is obtained, wherein the polyaminopolycarboxylic acid modified Abiraterone derivative has the following structure:

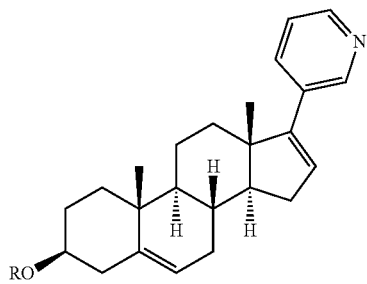

where, R=

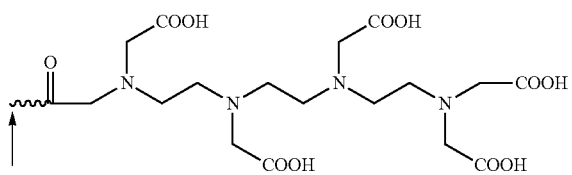

or

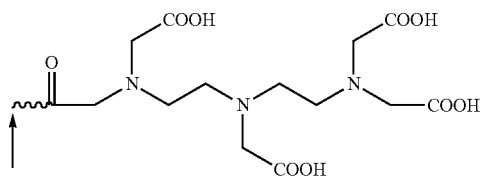

or

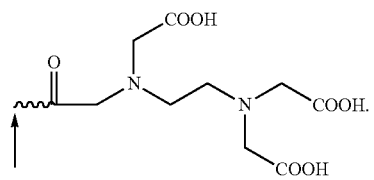

3. The method according to claim 2, further comprising the following steps: dissolving the Abiraterone and the polyaminopolycarboxylic acid monoanhydride with molar equivalent being 1.1-3 times that of Abiraterone in N,N-dimethylformamide or N-methyl pyrrolidone or dimethyl sulfoxide, reacting at a temperature of −10-40° C. for 5 to 48 hours under a condition of the alkaline catalyst, after reacting completely, performing suction filtration to remove an insoluble substance, adding glacial ether to a filtrate, standing at a temperature of −40° C. for more than 2 hours until a precipitate is completely separated out, collecting the precipitate via centrifugation, dissolving the precipitate in a mixed solution of water and acetonitrile, extracting with ether, collecting an aqueous phase, freeze-drying the aqueous phase, and obtaining the polyaminopolycarboxylic acid modified Abiraterone derivative.

4. A pharmaceutical preparation of a polyaminopolycarboxylic acid modified Abiraterone derivative, wherein the polyaminopolycarboxylic acid modified Abiraterone derivative according to claim 1 is prepared into freeze-dried powder for intravenous injection.

5. The pharmaceutical preparation of the polyaminopolycarboxylic acid modified Abiraterone derivative according to claim 4, comprising the following components: the polyaminopolycarboxylic acid modified Abiraterone derivative as an active ingredient, a freeze-dried excipient, a cosolvent, an emulsifying cosolvent, and an anti-oxidant.

6. The pharmaceutical preparation of the polyaminopolycarboxylic acid modified Abiraterone derivative according to claim 5, wherein the freeze-dried excipient is mannitol or glucose, the cosolvent is sodium bicarbonate or sodium carbonate or potassium carbonate or sodium hydroxide or potassium hydroxide, the emulsifying cosolvent is glycerin or polyethylene glycol with molecular weight of 300 or 400 or propylene glycol, and the anti-oxidant is sodium hydrogensulfite or sodium sulfite or sodium thiosulphate.

7. A method of treating a tumor comprising administering the polyaminopolycarboxylic acid modified Abiraterone derivative according to claim 1.

8. The method according to claim 7, wherein the tumor is prostate cancer.

9. The pharmaceutical preparation of claim 4, wherein the polyaminopolycarboxylic acid modified Abiraterone derivative is prepared by reacting Abiraterone with polyaminopolycarboxylic acid monoanhydride under an action of an alkaline catalyst at a ratio of 1:1.1-1:3, wherein the polyaminopolycarboxylic acid modified Abiraterone derivative has the following structure:

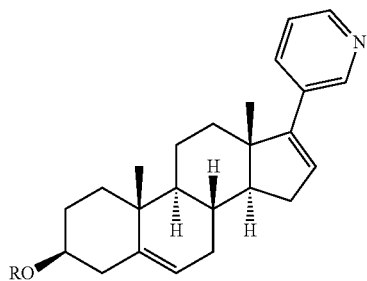

where, R=

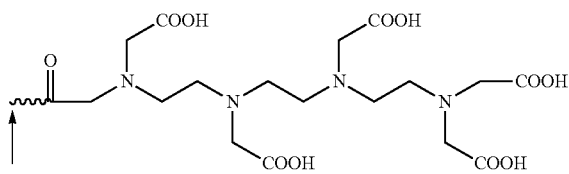

or

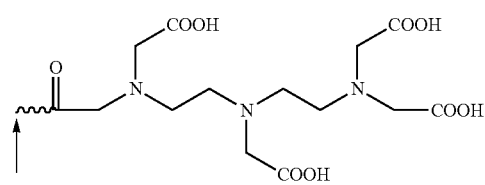

or

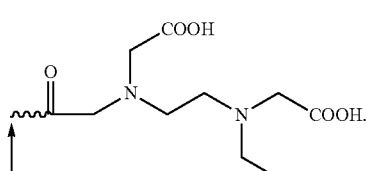

10. The pharmaceutical preparation of claim 9, wherein the polyaminopolycarboxylic acid modified Abiraterone derivative is prepared by a method comprising the following steps: dissolving the Abiraterone and the polyaminopolycarboxylic acid monoanhydride with molar equivalent being 1.1-3 times that of Abiraterone in N,N-dimethylformamide or N-methyl pyrrolidone or dimethyl sulfoxide, reacting at a temperature of −10-40° C. for 5 to 48 hours under a condition of the alkaline catalyst, after reacting completely, performing suction filtration to remove an insoluble substance, adding glacial ether to a filtrate, standing at a temperature of −40° C. for more than 2 hours until a precipitate is completely separated out, collecting the precipitate via centrifugation, dissolving the precipitate in a mixed solution of water and acetonitrile, extracting with ether, collecting an aqueous phase, freeze-drying the aqueous phase, and obtaining the polyaminopolycarboxylic acid modified Abiraterone derivative.

11. The method of claim 7, wherein the polyaminopolycarboxylic acid modified Abiraterone derivative is prepared by reacting Abiraterone with polyaminopolycarboxylic acid monoanhydride under an action of an alkaline catalyst at a ratio of 1:1.1-1:3, wherein the polyaminopolycarboxylic acid modified Abiraterone derivative has the following structure:

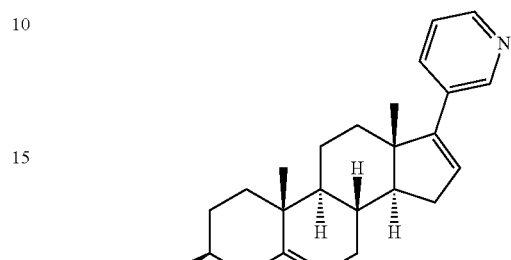

where, R=

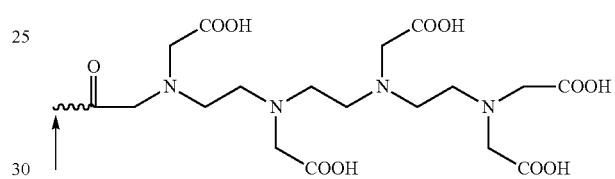

or

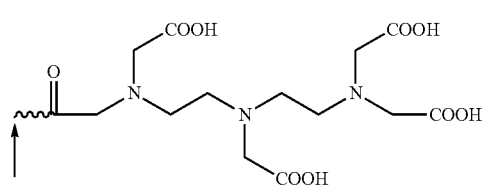

or

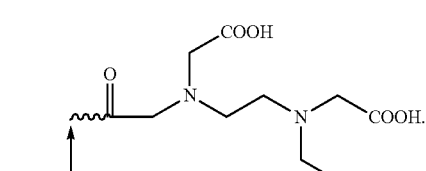

12. The method of claim 11, wherein the polyaminopolycarboxylic acid modified Abiraterone derivative is prepared by a method comprising the following steps: dissolving the Abiraterone and the polyaminopolycarboxylic acid monoanhydride with molar equivalent being 1.1-3 times that of Abiraterone in N,N-dimethylformamide or N-methyl pyrrolidone or dimethyl sulfoxide, reacting at a temperature of −10-40° C. for 5 to 48 hours under a condition of the alkaline catalyst, after reacting completely, performing suction filtration to remove an insoluble substance, adding glacial ether to a filtrate, standing at a temperature of −40° C. for more than 2 hours until a precipitate is completely separated out, collecting the precipitate via centrifugation, dissolving the precipitate in a mixed solution of water and acetonitrile, extracting with ether, collecting an aqueous phase, freeze-drying the aqueous phase, and obtaining the polyaminopolycarboxylic acid modified Abiraterone derivative.

13. The method of claim 7 wherein the polyaminopolycarboxylic acid modified Abiraterone derivative is prepared into freeze-dried powder for intravenous injection.

14. The method of claim 13, wherein the Abiraterone derivative is administered as a composition comprising the following components: the polyaminopolycarboxylic acid modified Abiraterone derivative as an active ingredient, a freeze-dried excipient, a cosolvent, an emulsifying cosolvent, and an anti-oxidant.

15. The method of claim 14, wherein the freeze-dried excipient is mannitol or glucose, the cosolvent is sodium bicarbonate or sodium carbonate or potassium carbonate or sodium hydroxide or potassium hydroxide, the emulsifying cosolvent is glycerin or polyethylene glycol with molecular weight of 300 or 400 or propylene glycol, and the anti-oxidant is sodium hydrogensulfite or sodium sulfite or sodium thiosulphate.

\* \* \* \* \*